(12) United States Patent
Hellbusch et al.

(10) Patent No.: US 9,759,637 B1
(45) Date of Patent: Sep. 12, 2017

(54) SOIL SAMPLER

(71) Applicants: James A. Hellbusch, Columbus, NE (US); Todd Stachura, Columbus, NE (US)

(72) Inventors: James A. Hellbusch, Columbus, NE (US); Todd Stachura, Columbus, NE (US)

(73) Assignee: DUO LIFT MANUFACTURING CO., INC., Columbus, NE (US)

( * ) Notice: Subject to any disclaimer, the term of this patent is extended or adjusted under 35 U.S.C. 154(b) by 104 days.

(21) Appl. No.: 14/884,165

(22) Filed: Oct. 15, 2015

(51) Int. Cl.
*G01N 1/04* (2006.01)
*G01N 1/08* (2006.01)
*G01N 33/24* (2006.01)

(52) U.S. Cl.
CPC ............... *G01N 1/08* (2013.01); *G01N 33/24* (2013.01); *G01N 2033/245* (2013.01)

(58) Field of Classification Search
CPC ............................ G01N 1/08; G01N 2033/245
USPC .................. 73/864.74; 111/95–98, 135, 136; 414/442; 175/20
See application file for complete search history.

(56) References Cited

U.S. PATENT DOCUMENTS

| | | | | |
|---|---|---|---|---|
| 5,394,949 A | * | 3/1995 | Wright et al. | .......... E21B 7/006 175/121 |
| 5,435,399 A | * | 7/1995 | Peterson et al. | .......... E02D 1/04 175/135 |
| 6,360,829 B1 | | 3/2002 | Naber et al. | |
| 6,363,803 B1 | * | 4/2002 | Hubers | ................... E21B 49/02 175/19 |
| 7,255,016 B2 | | 8/2007 | Burton | |
| 7,827,873 B2 | | 11/2010 | Burton | |
| 8,955,401 B1 | | 2/2015 | Burton | |
| 2016/0090788 A1 | * | 3/2016 | Niemczyk | ............... E21B 7/023 175/162 |

* cited by examiner

*Primary Examiner* — Lisa Caputo
*Assistant Examiner* — Roger Hernandez-Prewitt
(74) *Attorney, Agent, or Firm* — Dennis L. Thomte; Thomte Patent Law Office LLC

(57) ABSTRACT

A trailer mounted soil sampler including one or more soil sampling assemblies mounted thereon. Each of the soil sampler assemblies being selectively pivotally movable between horizontally disposed and vertically disposed positions. Each of the soil sampling assemblies includes an elongated hollow soil probe which is driven into the ground to collect a soil sample therein. The soil sampler includes a soil cleaning and oiler mechanism. The soil sampler also includes a trash cleaner for cleaning trash from the area where the soil probe is to be driven into the ground. Further, the soil sampler includes a soil sample collection apparatus for collecting the soil samples in bags.

9 Claims, 18 Drawing Sheets

SOIL SAMPLER

CROSS REFERENCE TO RELATED APPLICATION

This is a Non-Provisional Application of Application Ser. No. 64/240,245 filed on Oct. 12, 2015 entitled SOIL SAMPLER.

BACKGROUND OF THE INVENTION

Field of the Invention

This invention relates to a soil sampler device which may be mounted on a trailer or on a vehicle such as a truck, ATV, UTV, etc. This invention more particularly relates to a soil sampler which is configured to remove and collect sample cores from agricultural fields to enable the landowner to determine whether there is a need to apply certain nutrients to the soil. Even more particularly, this invention relates to an improved soil sampler.

Description of the Related Art

It is the objective of agriculture to optimize the productive capacity of land designated for a particular purpose. The grower will, therefore, attempt to provide, in each plot of soil, the amount of fertilizer and other nutrients and additives that will render the plot ideal for the crop that is to be sown. The harvest taken from the land is, thereby, maximized. A grower, not having information as to the constituency of the soil, may not properly utilize agents applied to the field. If the grower is ignorant of what the current status of nutrients in the soil is, he cannot know how much fertilizer or other additives should be infused into the field.

The amount of existent nutrients and minerals will vary over time. A number of factors will bear upon how the soil is to be treated. These include prior applicants and history of prior-grown crops and previously applied additives. It is for these reasons that soil sampling is important.

Sampling of the soil can even be critical. The importance of testing soil samples is certainly readily apparent to the grower. It is, therefore, typical for the grower to take samples from various locations on an agricultural field. The samples consist of multiple soil extractions or "cores" obtained using probes at particular locations in the field. These samples are then analyzed to determine the level of the various nutrients and minerals. It is also important to know the level of compaction of the soil in various regions.

Solutions have been proposed to improve and make more efficient the process of taking soil samples. U.S. Pat. No. 7,827,873, issued to James D. Burton on Nov. 9, 2010 for an invention entitled SOIL SAMPLING APPARATUS AND METHOD, for example, illustrates an apparatus which automatically collects soil samples. The apparatus is run over a field where certain information is sought to be obtained. The apparatus includes a sampling assembly that rotates on a track. The probe of the assembly extends through the track and into the ground. The probe is retracted on each revolution of the track. The assembly is hinged and guided along the track in order to minimize soil compaction as the probe rotates around the rear wheel of the apparatus. Soil cores are pneumatically transferred to a bagging assembly which is located in the tractor or other vehicle which pulls the sampling apparatus.

The apparatus of the '873 patent, however, has distinct shortcomings. Particularly relevant is the distribution of probes taken at the various locations in the field.

Assignee's earlier patent application, Ser. No. 13/852,790 filed Mar. 28, 2013, represented an improvement in the soil sampling art. The instant invention relates to an improvement of Assignee's earlier invention.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

The soil sampler of this invention includes a support frame having a forward end, a rearward end, a first side and a second side. The support frame may be mounted on a wheeled frame such as a trailer or mounted on the bed of a truck, ATV, UTV, etc. A pair of soil sampler assemblies are mounted on the support frame. Further, only a single soil sampler assembly could be mounted on the support frame or a plurality of soil sampling assemblies could be mounted on the support frame, if desired. For purposes of conciseness, the soil sampler will be described in this summary as having a single soil sampler assembly mounted thereon.

An elongated first support having a first end and a second end is pivotally secured intermediate its length, to the support frame about a horizontal axis which is transversely disposed with respect to the longitudinal axis of the first support. The first support is selectively pivotally movable with respect to the support frame between a generally horizontally disposed first position and a vertically disposed second position. The soil sampler assembly includes a first pneumatic cylinder having an elongated barrel, with forward and rearward ends, and a piston rod which movably extends from the rearward end of the barrel thereof. The piston rod of the first pneumatic cylinder is movable between extended and retracted positions with respect to the barrel thereof. The forward end of the barrel of the first pneumatic cylinder is pivotally secured to the support frame. The piston rod of the first pneumatic cylinder is pivotally secured to the first support. The extension of the piston rod of the first pneumatic cylinder causes the first support to be pivotally moved from its horizontally disposed first position to its vertically disposed second position with respect to the support frame. The retraction of the piston rod of the first pneumatic cylinder causes the first support to be pivotally moved from its second position to its first position with respect to the support frame.

An elongated slide rail, having first and second ends, is mounted on the first support at the second end of the first support. The soil sampler assembly also includes a second pneumatic cylinder including an elongated barrel, with first and second ends, and a piston rod movably extending from the second end thereof. The first end of the barrel of the second pneumatic cylinder is operatively secured to the first support. A slide member is slidably mounted on the slide rail between first and second positions with respect thereto. The piston rod of the second pneumatic cylinder is selectively movable between retracted and extended positions with respect to the barrel of the second pneumatic cylinder. The piston rod of the second pneumatic cylinder is secured to the slide member. The soil sampler assembly also includes an air actuated hammer device which is secured to the slide member for movement with the slide member. The hammer device has a connector element extending therefrom. The slide member, when the piston rod of the second pneumatic cylinder is in the retracted position, is in the first position. The slide member, when the piston rod of the second pneumatic cylinder is in the extended position, is in the second position. The connector element of the hammer device is secured to an elongated hollow soil probe having first and second ends whereby movement of the slide member with respect to the first support causes movement of the soil probe between first and second positions. The soil probe is driven into the soil to be sampled by the extension of the piston rod of the second pneumatic cylinder when the first support is in its vertically disposed second position. The soil probe and the soil sample therein is raised upwardly from the soil being sampled, after the soil probe has been driven into the soil, by the retraction of the piston rod of the second pneumatic cylinder.

The soil sampler assembly also includes a soil pressure foot assembly which has a flat pressure foot having a soil probe opening formed therein whereby the soil probe extends through the soil probe opening in the pressure foot. A third pneumatic cylinder is operatively secured to the first support and the pressure food for moving the pressure foot between first and second positions. The pressure foot is in engagement with the soil being sampled when in its second position and the first support is in its vertically disposed position.

The soil sampler of this invention also includes a soil sample collection apparatus supported on the support frame for collecting soil samples from the soil probe. A soil probe cleaner and oiler is also provided. Further, a trash removal device is also provided.

It is therefore a principal object of the invention to provide an improved soil sampler.

A further object of the invention is to provide a soil sampler which may be mounted on a trailer or on a truck, ATV, UTV, etc.

A further object of the invention is to provide a soil sampler which represents a distinct improvement over the prior art soil sampler devices.

A further object of the invention is to provide a soil sampler which includes a soil probe cleaner and oiler mechanism.

A further object of the invention is to provide a soil sampler including an air hammer device which assists in driving the soil probe into hard ground.

A further object of the invention is to provide a soil sampler which includes a trash cleaner.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
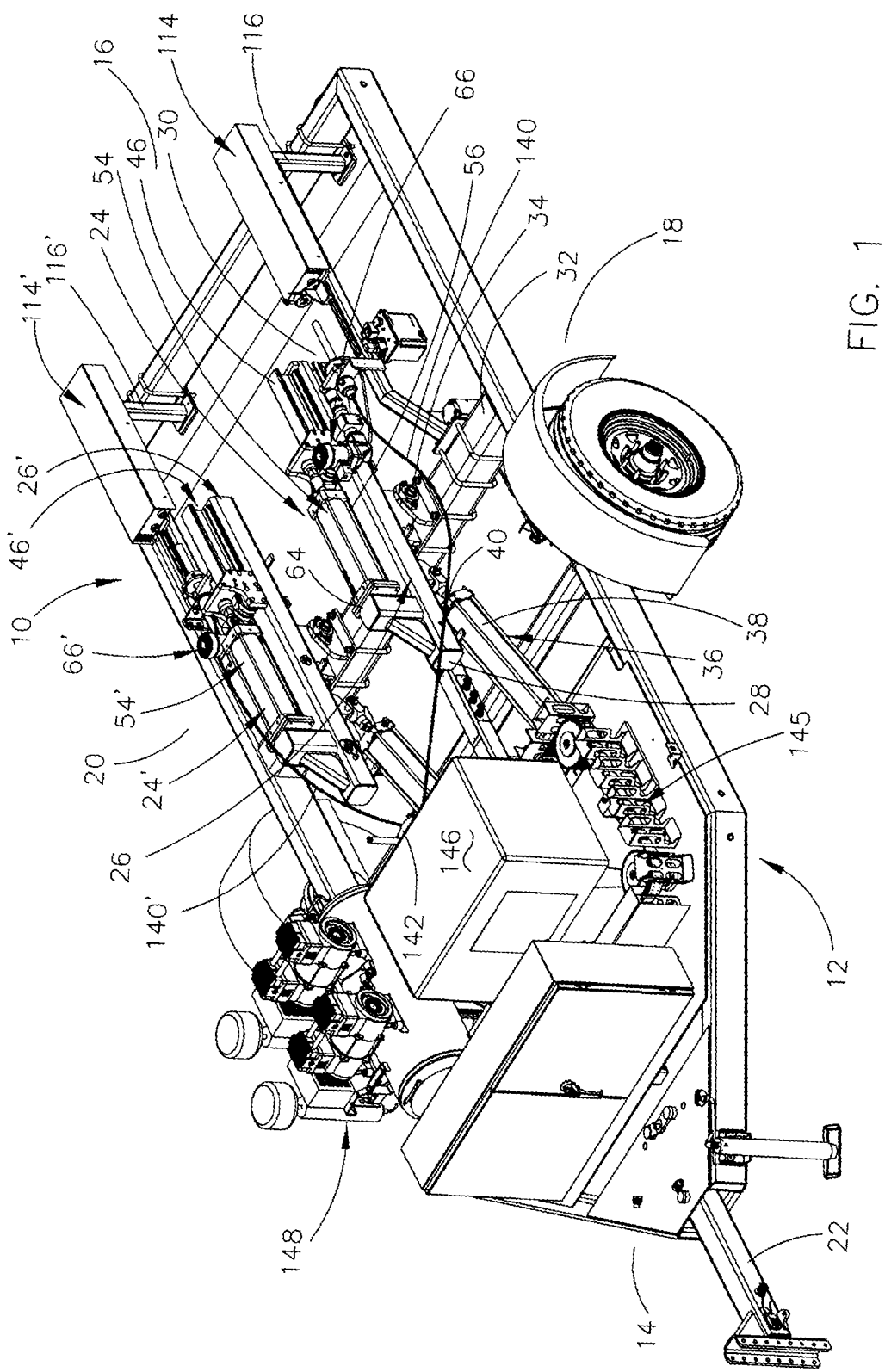
FIG. 1 is a front perspective view of the soil sampler of this invention.
Figure 2:
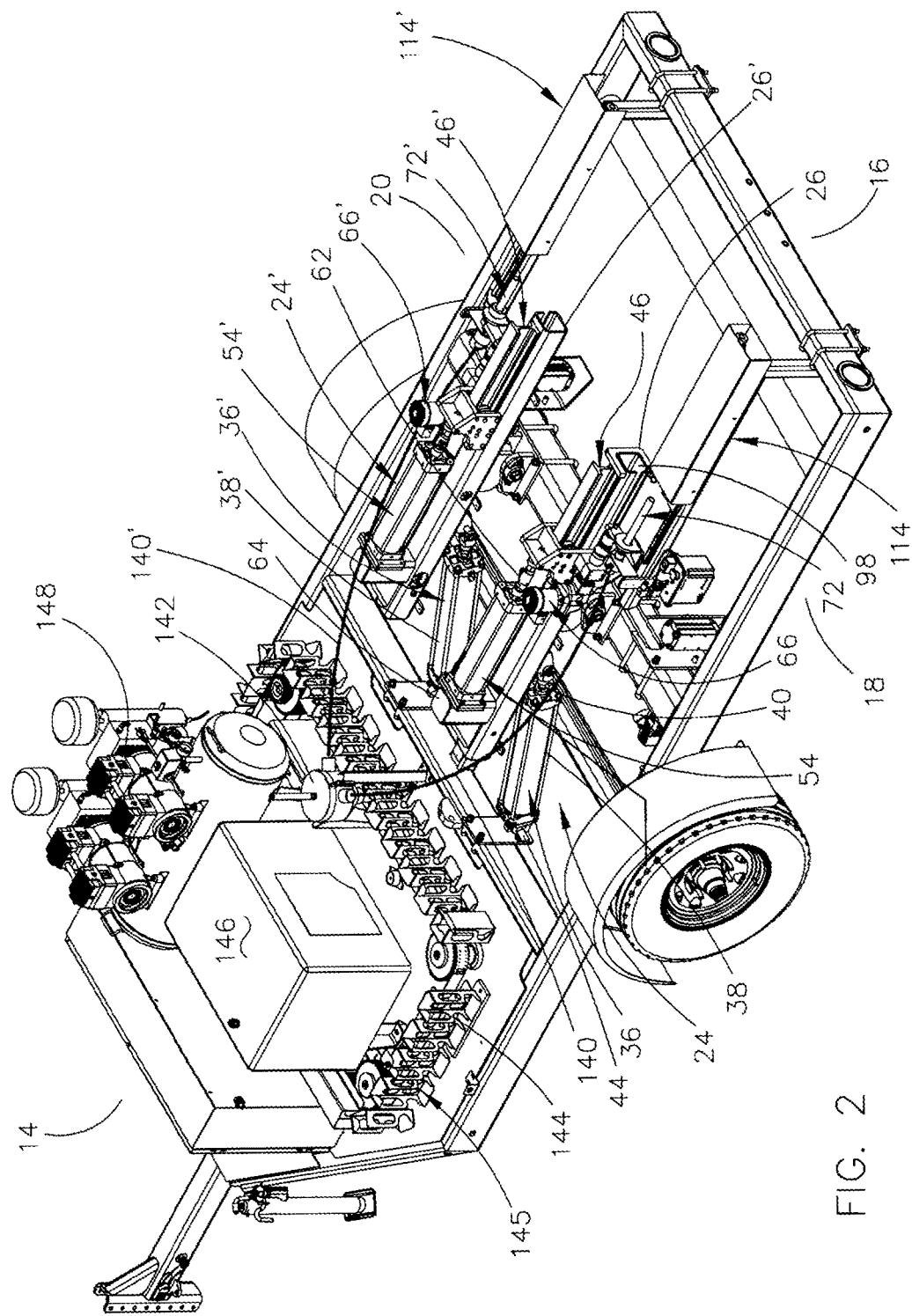
FIG. 2 is a rear perspective view of the soil sampler of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The soil sampler of this invention is referred to by the reference numeral 10. The drawings illustrate that the soil sampler 10 is mounted on a trailer but the soil sampler could be mounted in the bed of a truck if so desired. Soil sampler 10 includes structure for obtaining two soil samples. However, the soil sampler 10 could be designed to take one soil sample or a plurality of soil samples.

Soil sampler 10 includes a wheeled frame 12 having a forward end 14, a rearward end 16, a left side 18 and a right side 20. A hitch 22 extends forwardly from frame 12 for connection to a vehicle such as a truck, tractor, ATV or UTV. Soil sampler 10 includes two soil sampling assemblies 24 and 24'. Inasmuch as assemblies 24 and 24' are identical, only assembly 24 will be described in detail with "'" indicating identical structure on assembly 24'.

Figure 9:
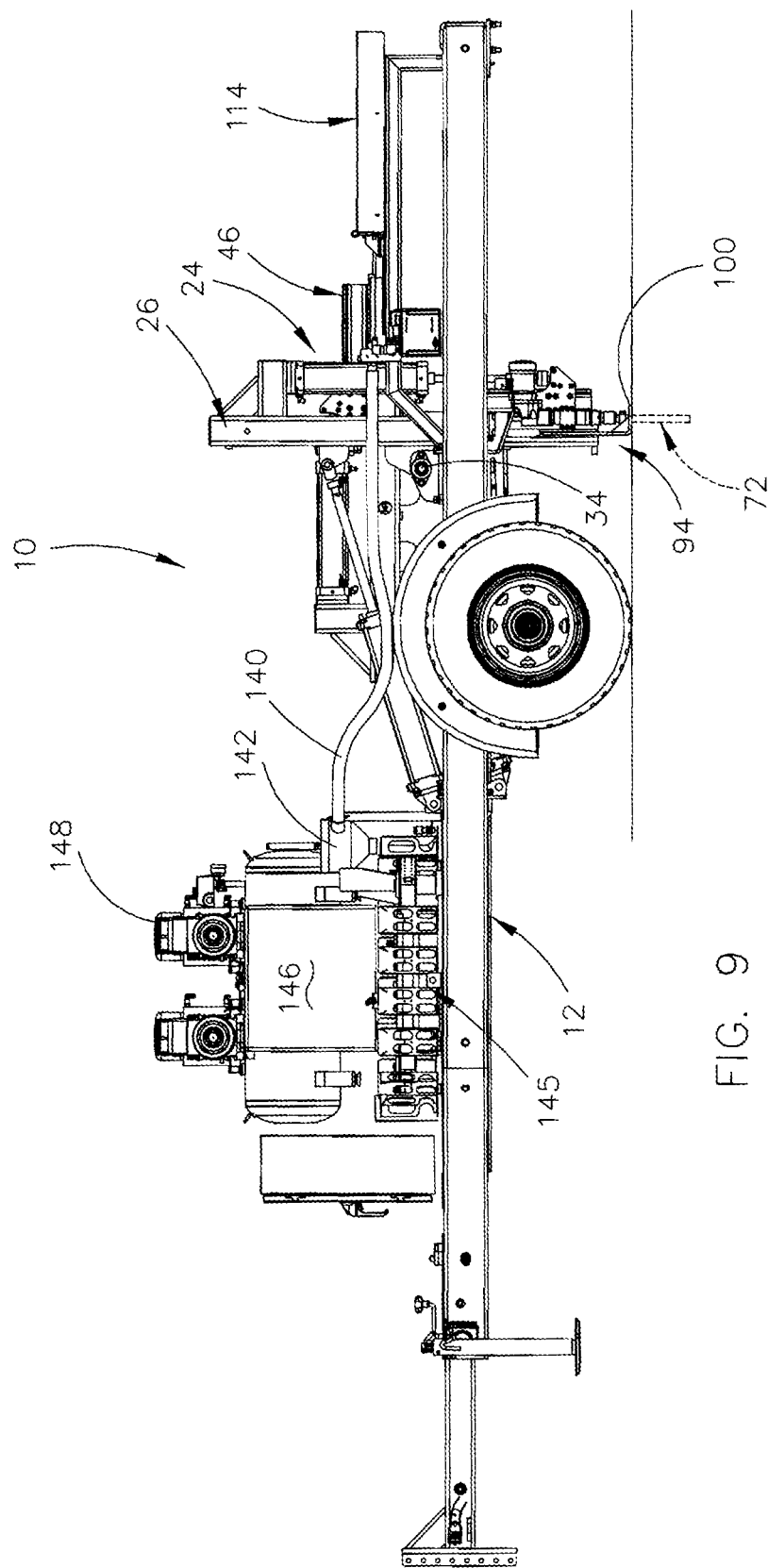
FIG. 9 is a left side view of the soil sampler of this invention with one of the soil sampler assemblies being in its operative position with the pressure foot thereof being in ground engagement and with the associated soil probe being moved downwardly into the soil.
Figure 10:
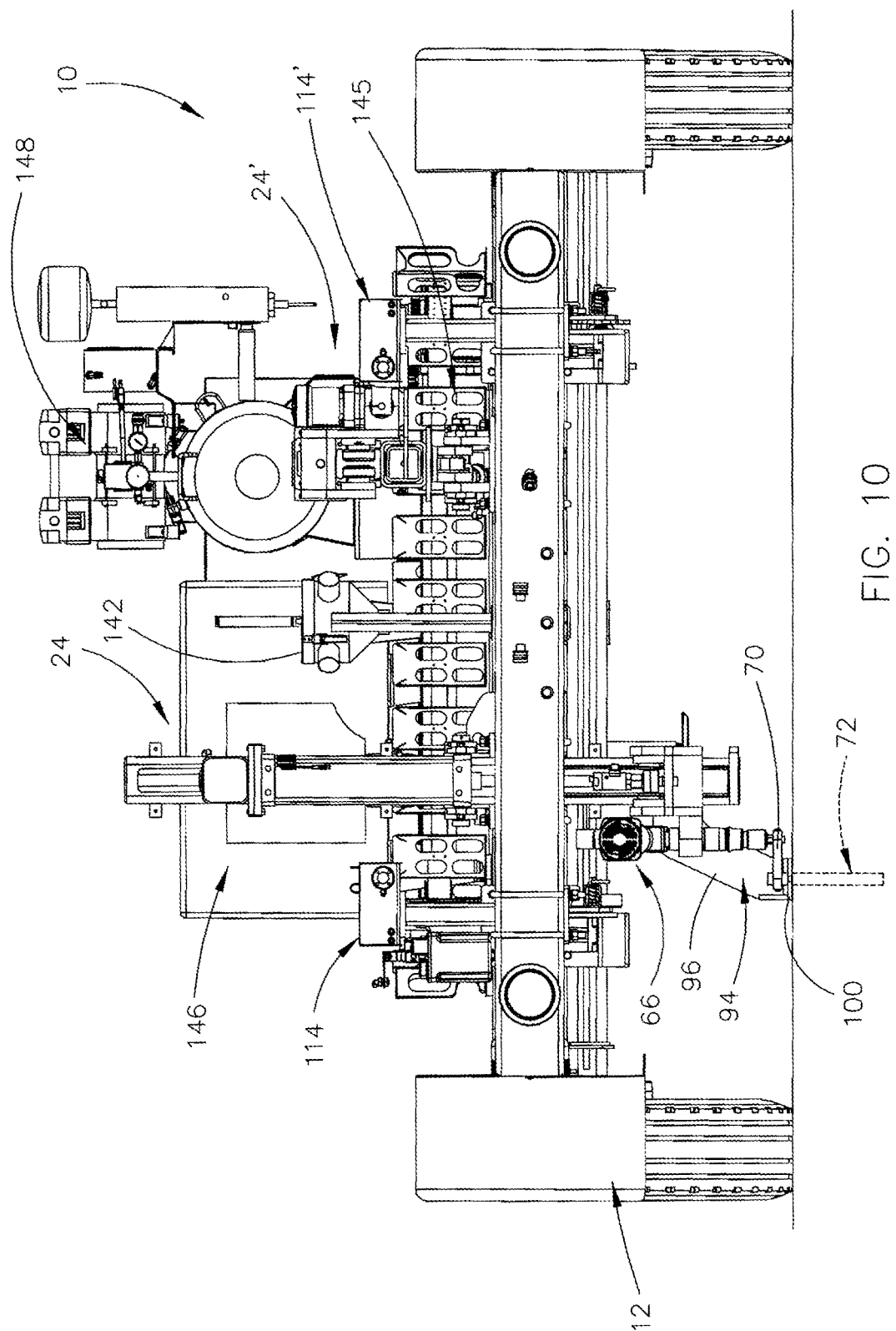
FIG. 10 is a rear view of the soil sampler of FIG. 9.
Figure 11:
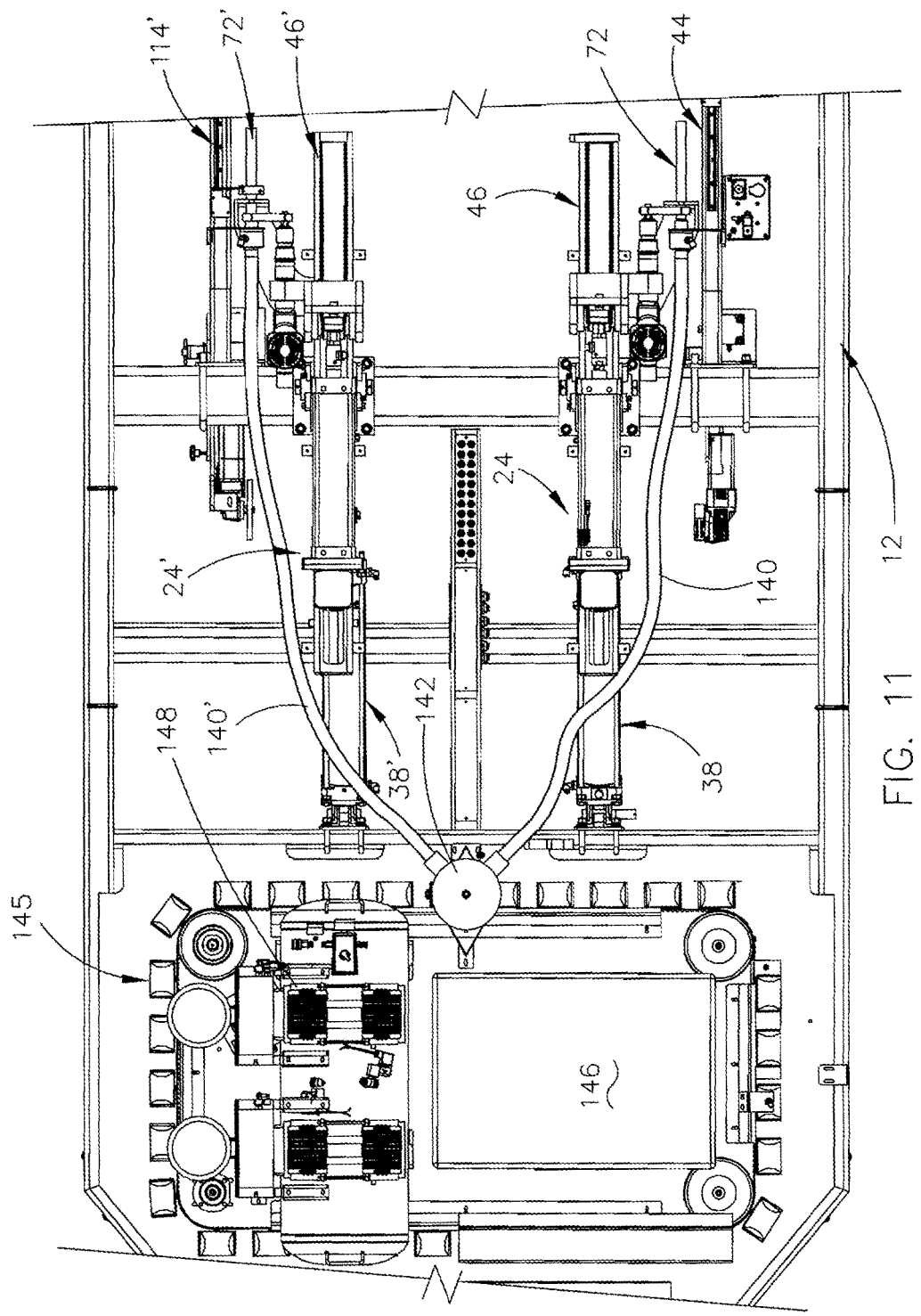
FIG. 11 is a partial top view of the soil sampler of this invention with both of the soil sampler assemblies thereof being in their stowed inoperative positions.
Figure 12:
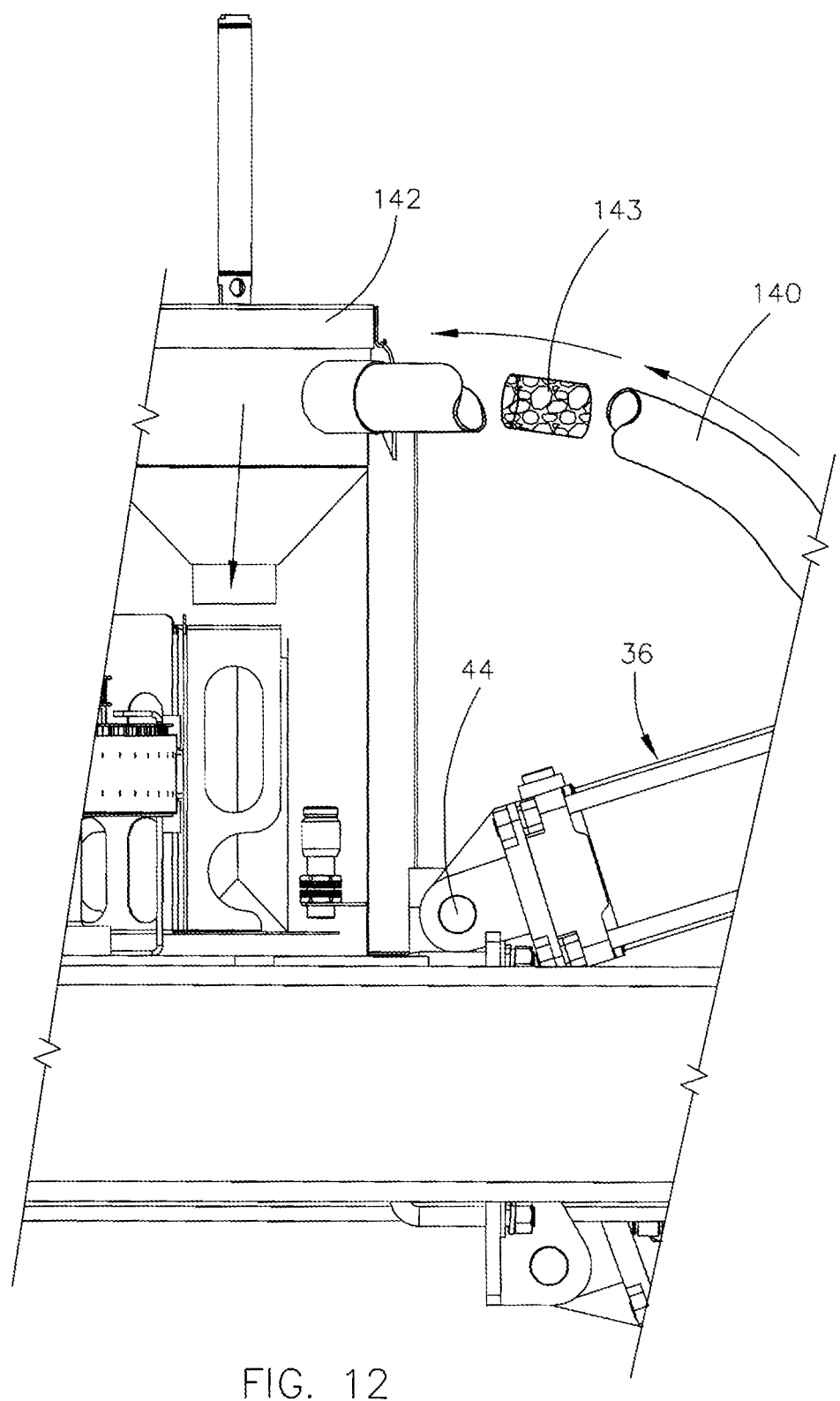
FIG. 12 is a partial view of the soil sampler of this invention illustrating a soil sampler being conveyed to the sampler distributor portion of the invention.
Figure 13:
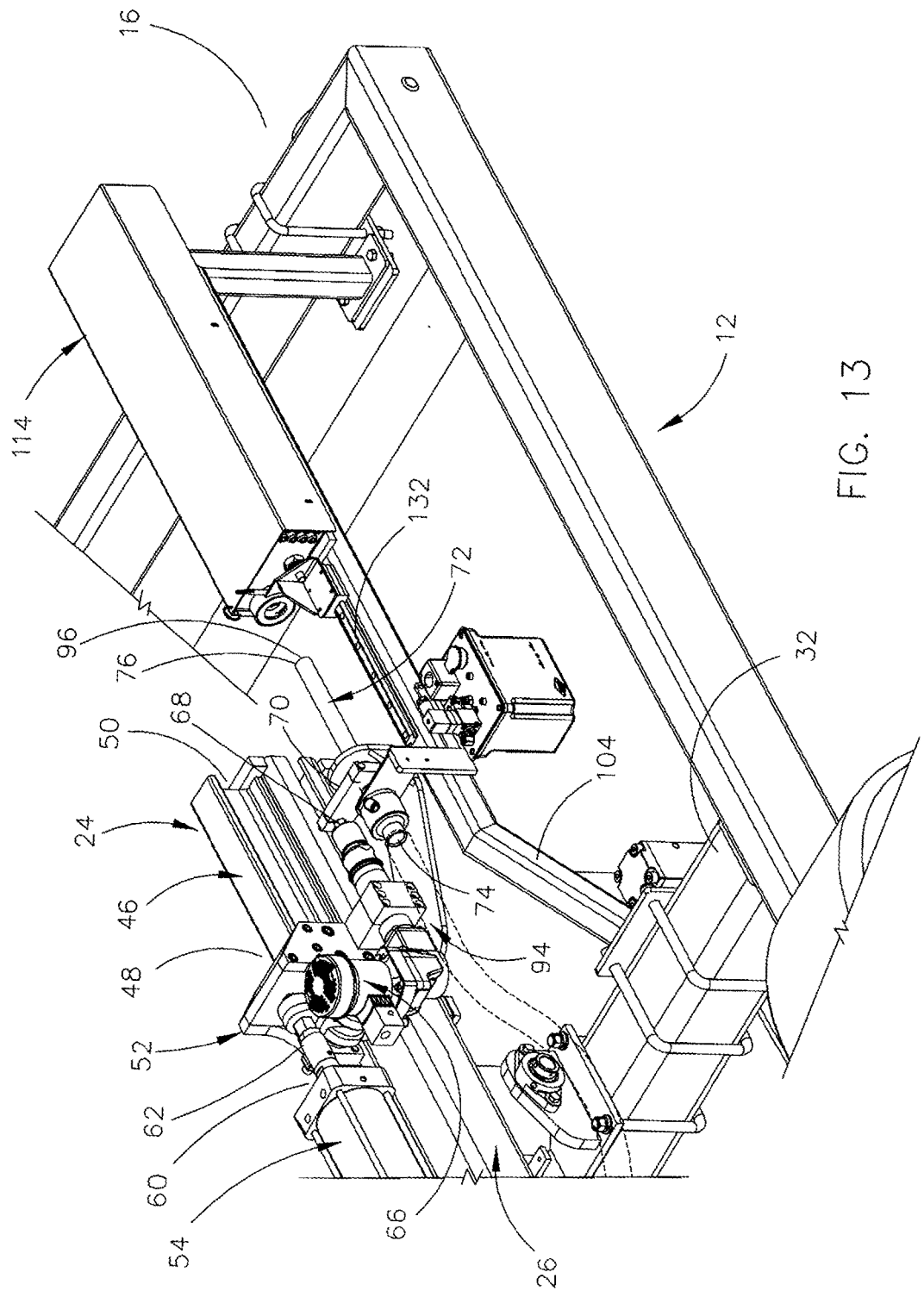
FIG. 13 is a partial perspective view illustrating one of the soil sampler assemblies in its stowed position after the soil probe has collected a soil core.
Figure 14:
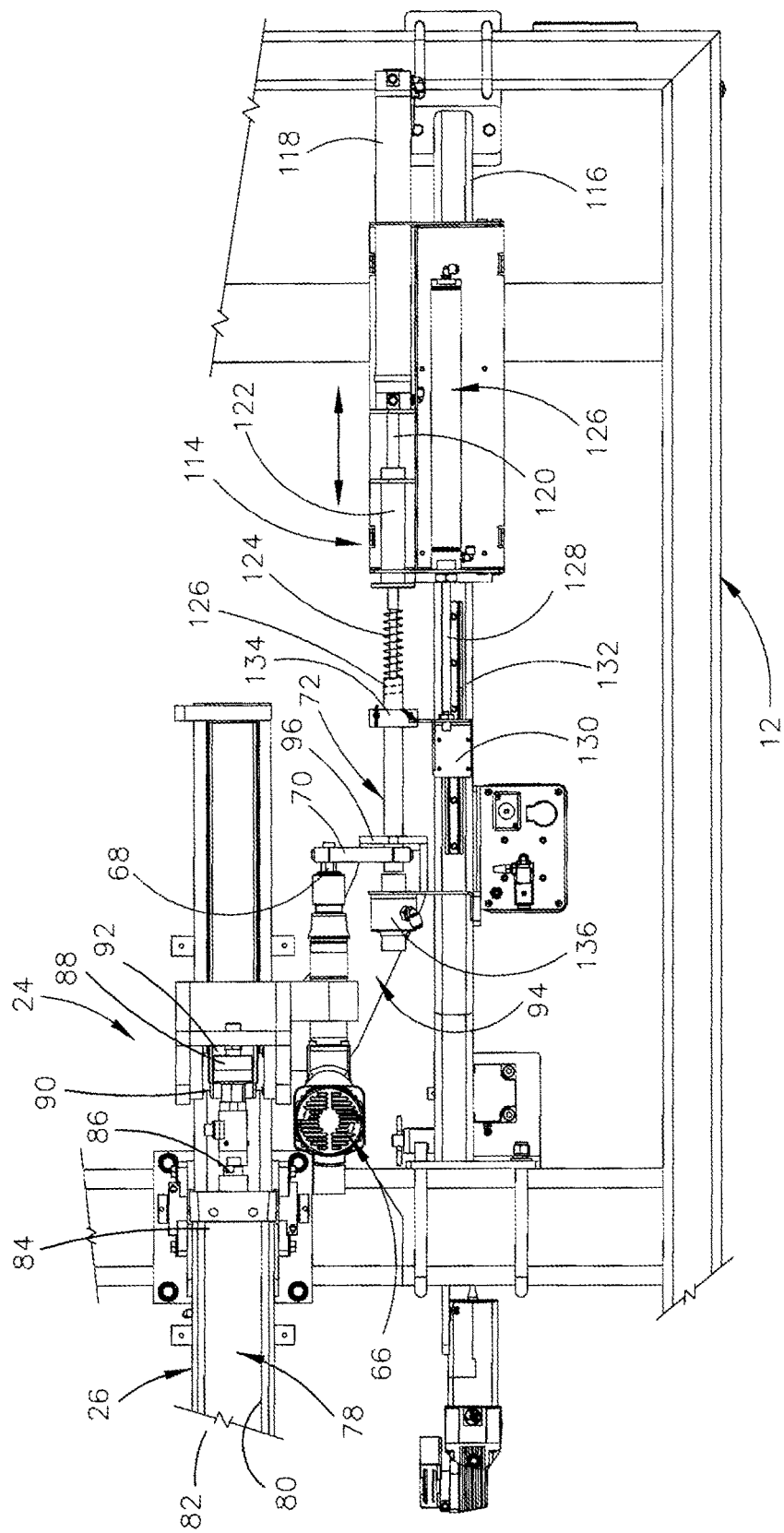
FIG. 14 is a partial top view which illustrates the mechanism which pushes the soil core from the soil probe.
Figure 15:
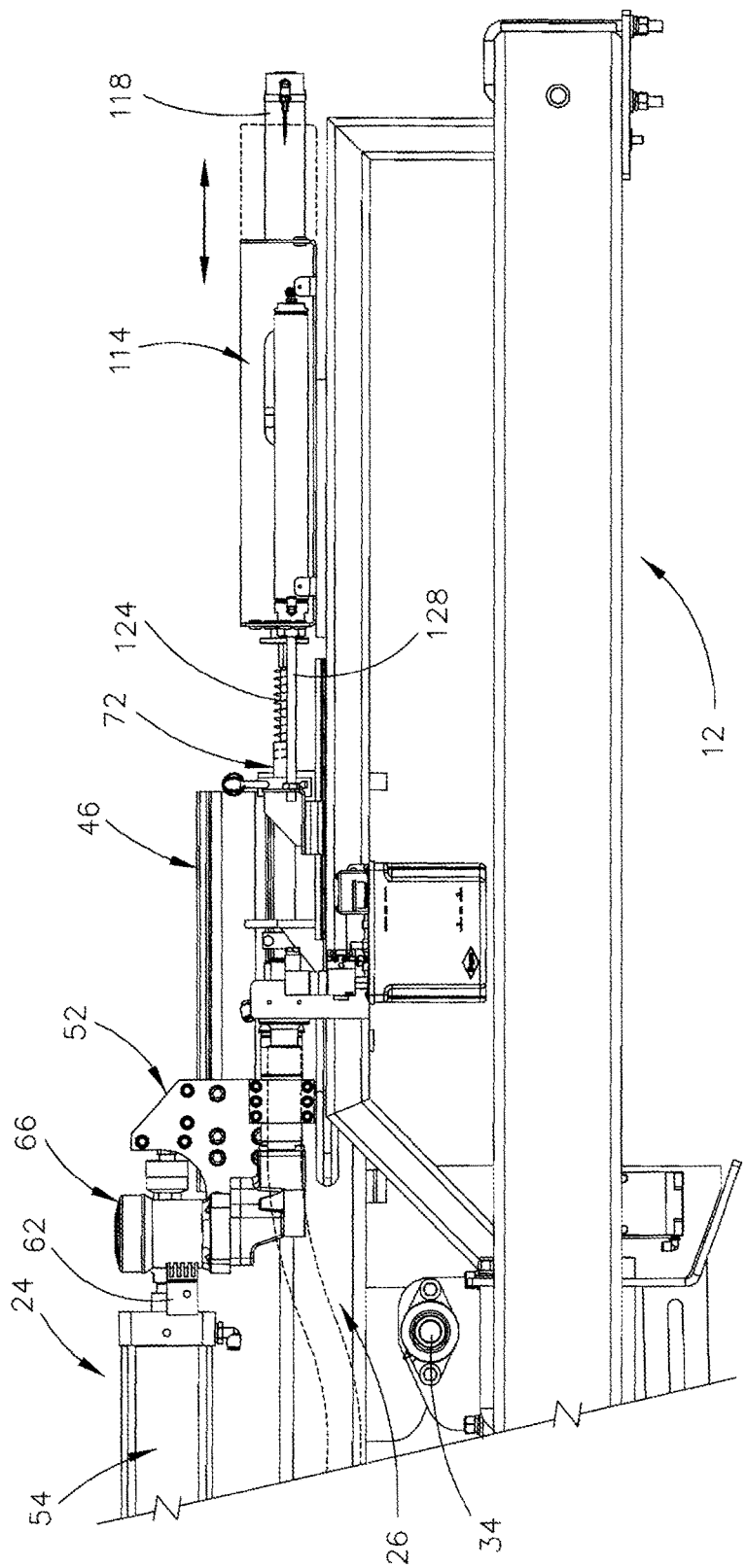
FIG. 15 is a partial side view which illustrates the mechanism which pushes the soil core from the soil probe.

The numeral 26 refers to an elongated support having a first end 28 and a second end 30. Support 26 is pivotally secured intermediate its ends 28 and 30 to cross-member 32 of frame 12 by a pivot pin 34 which is transversely disposed with respect to support 26. Support 26 is selectively pivotally movable between a horizontally disposed first position (FIG. 1) to a vertically disposed second position (FIG. 9) with respect to frame 12.

Figure 3:
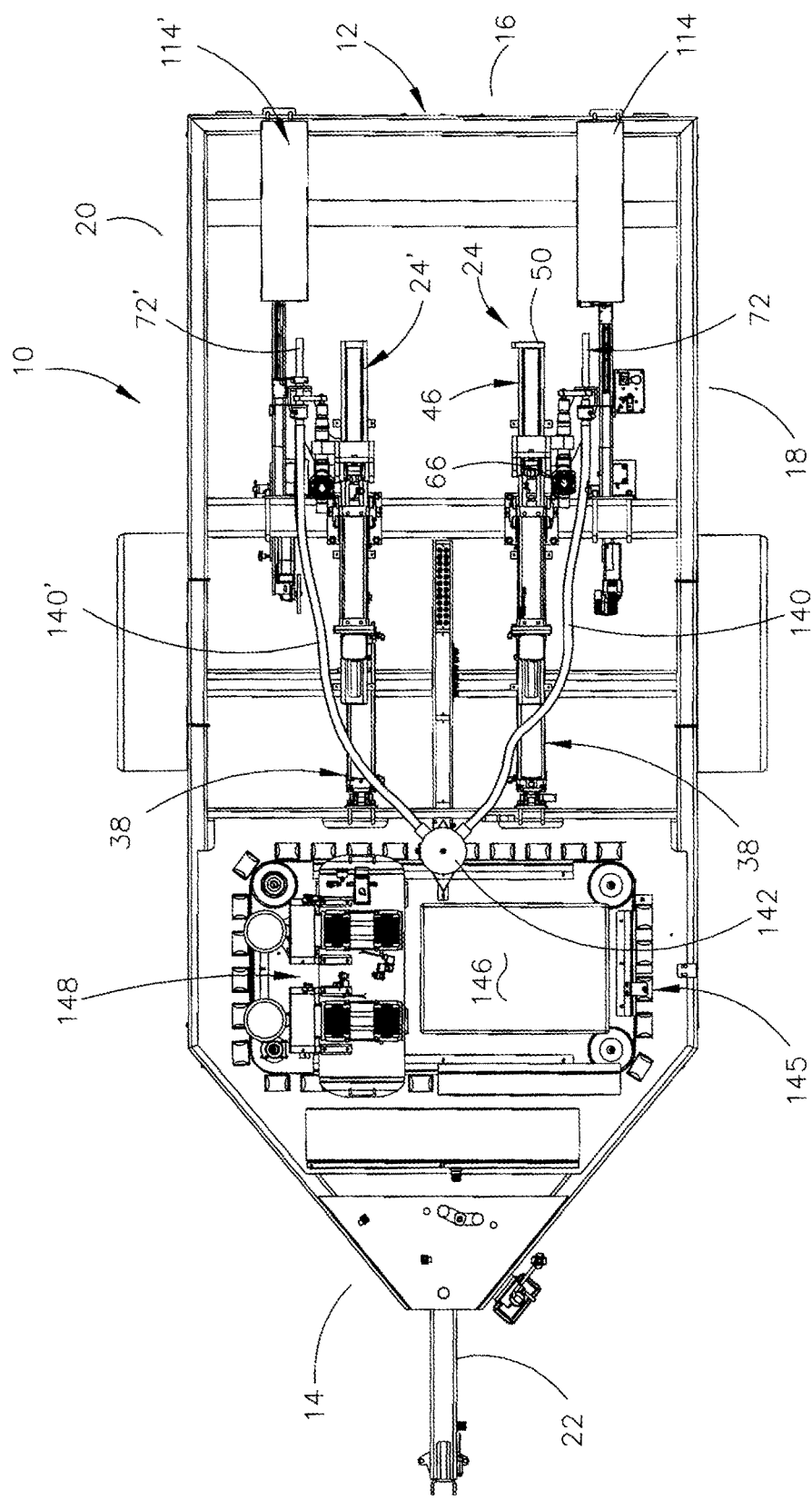
FIG. 3 is a top view of the soil sampler of this invention.
Figure 4:
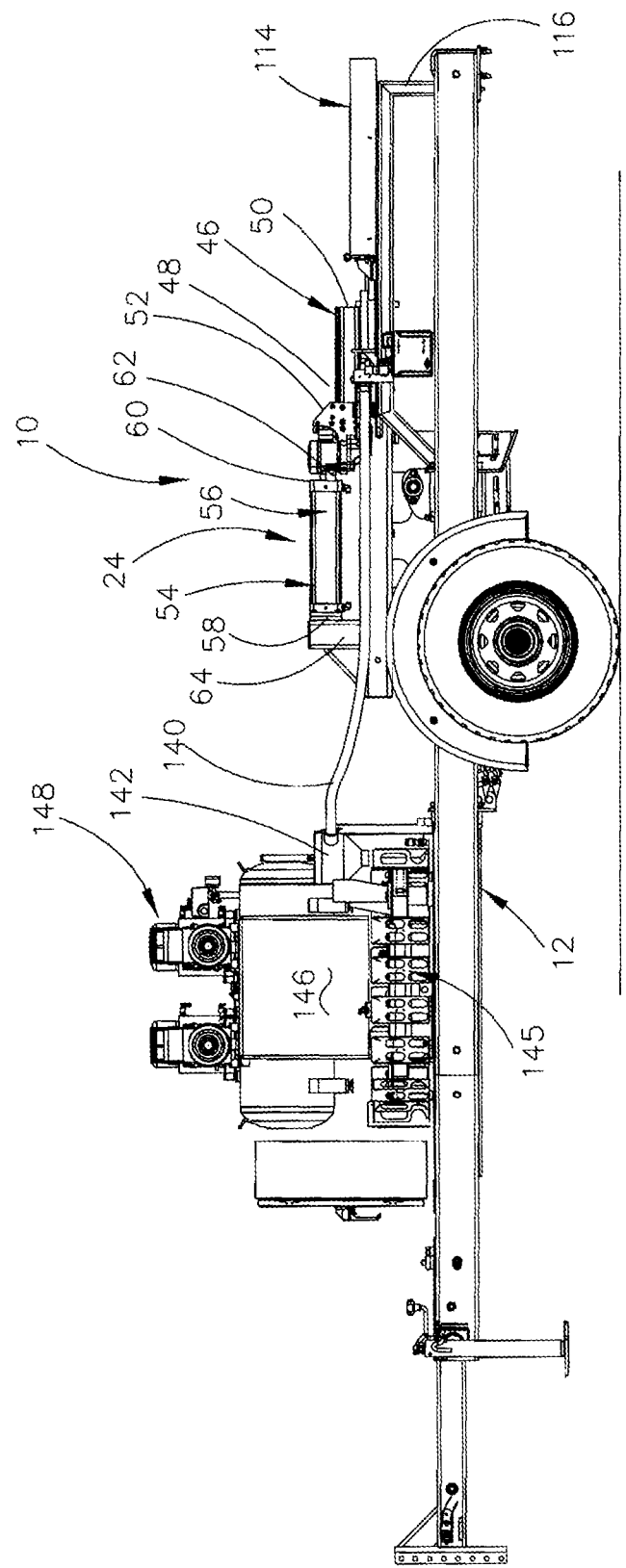
FIG. 4 is a left side view of the soil sampler of this invention.
Figure 5:
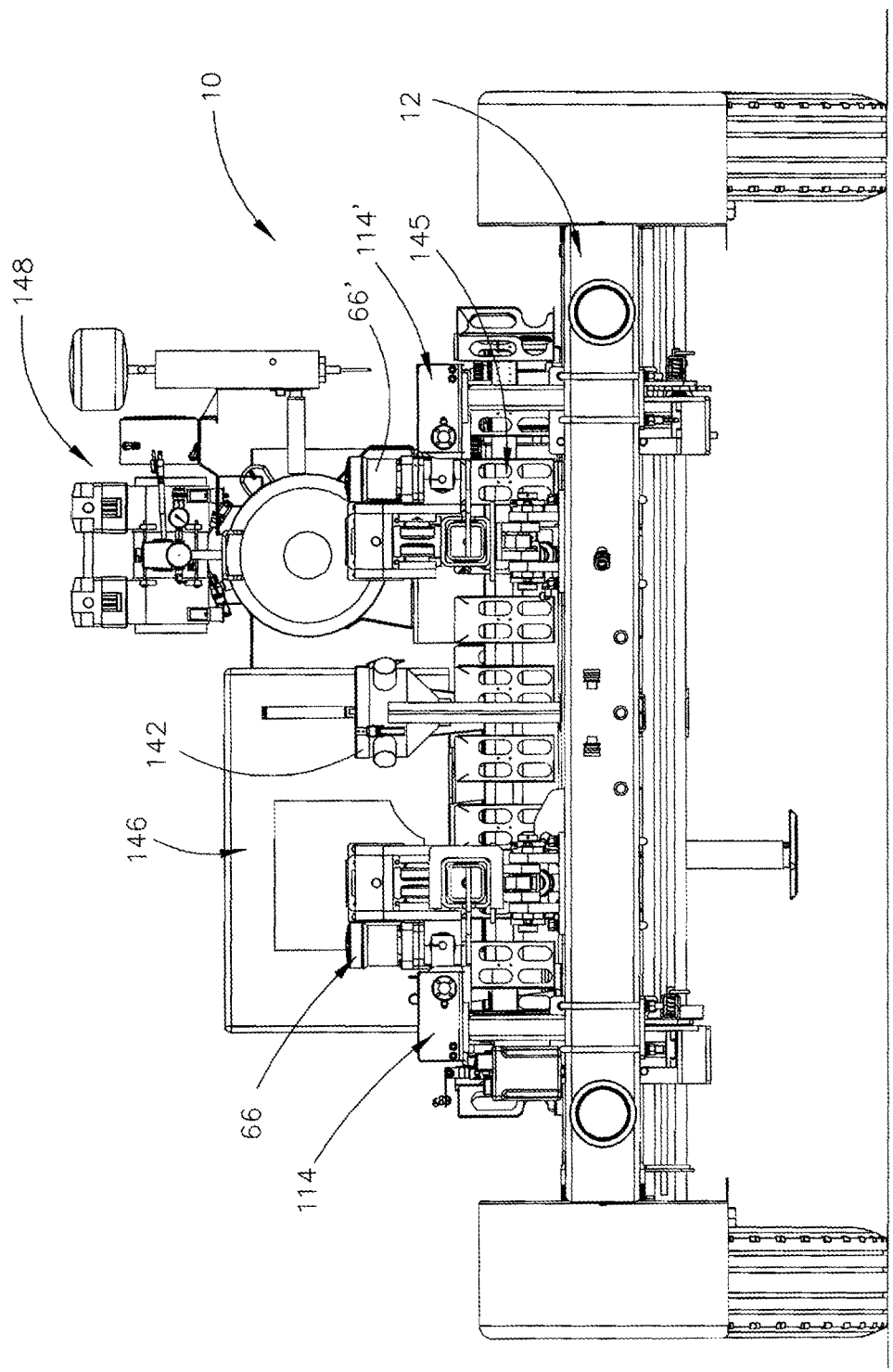
FIG. 5 is a rear view of the soil sampler of this invention.
Figure 6:
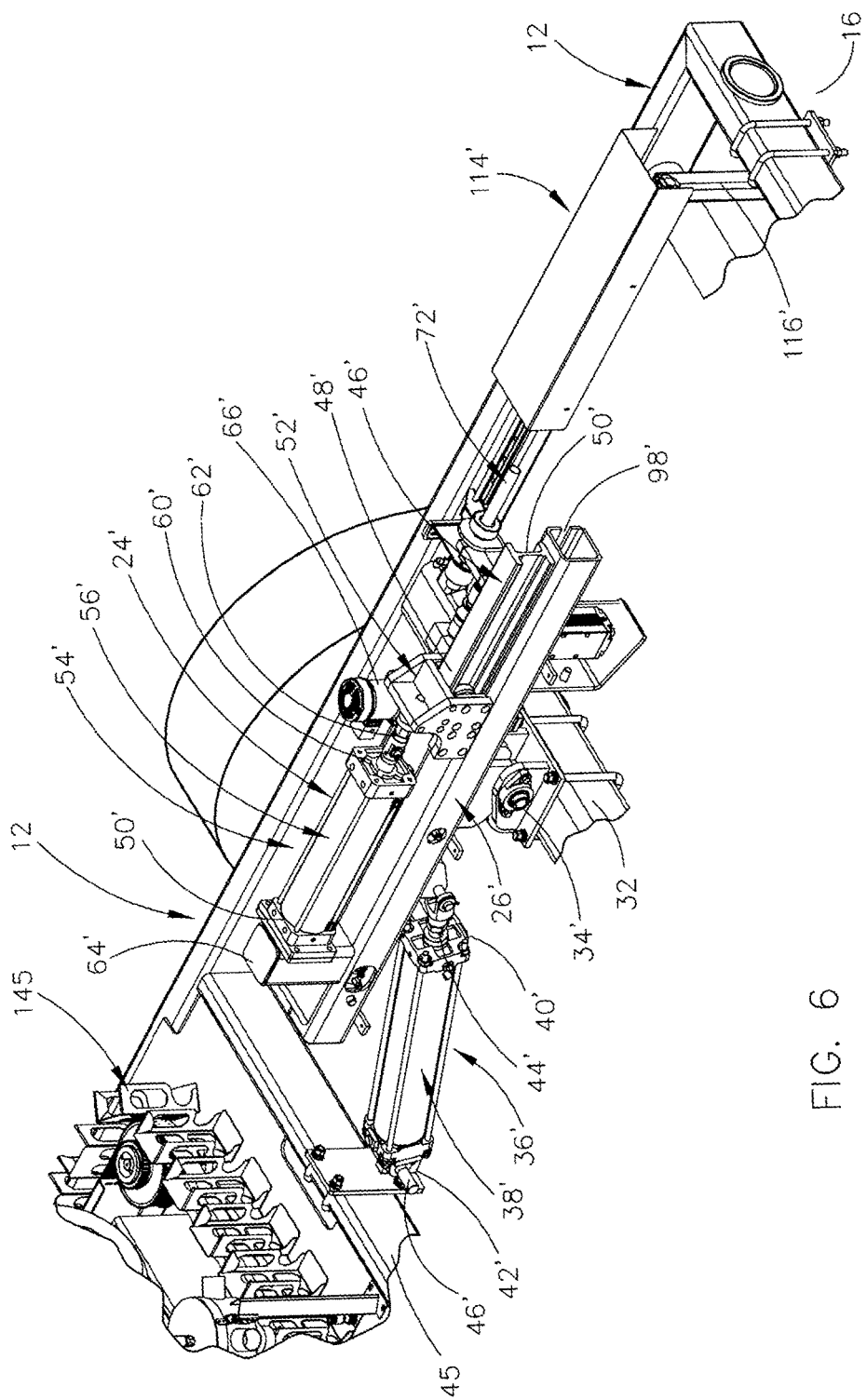
FIG. 6 is a partial rear perspective view of the soil sampler of this invention.
Figure 7:
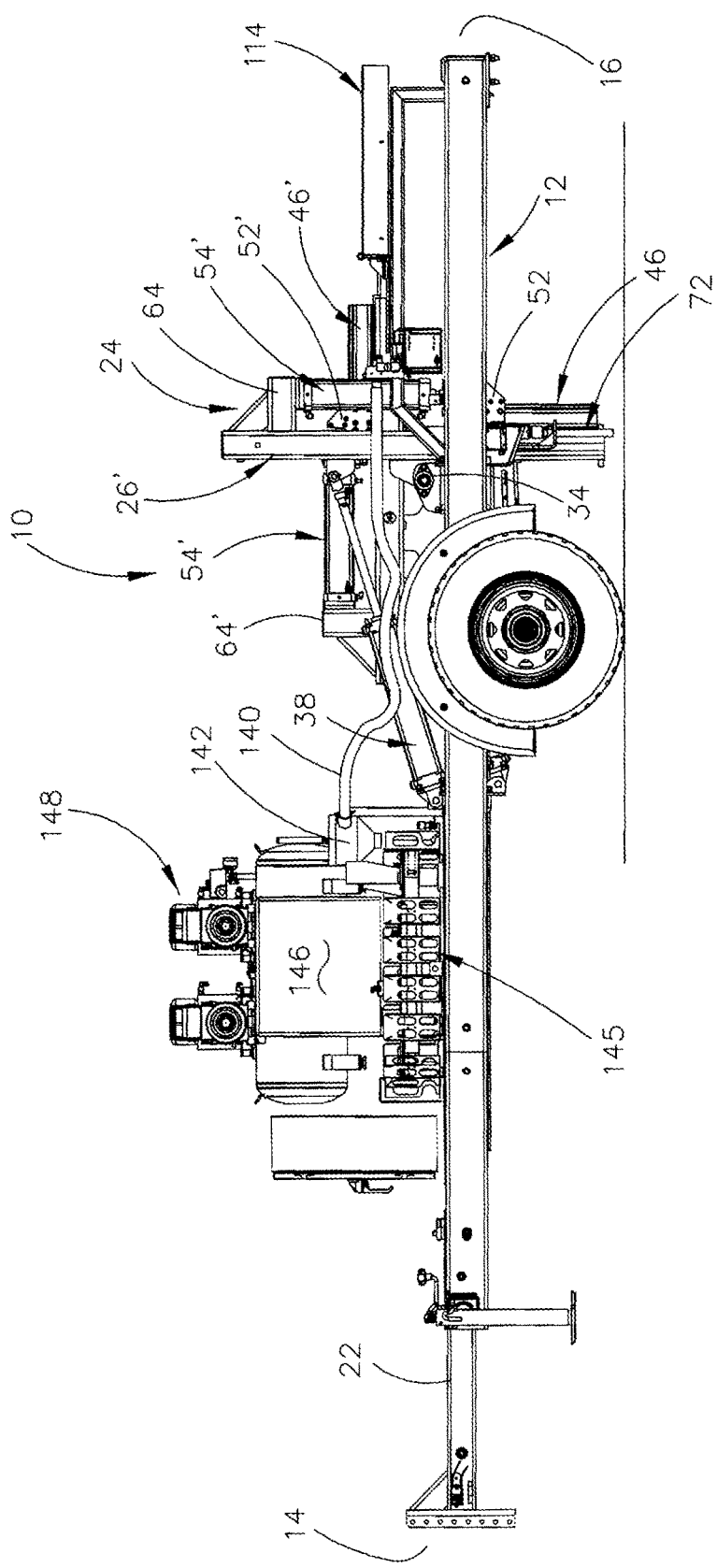
FIG. 7 is a left side view of the soil sampler of this invention which is similar to FIG. 4 except that one of the soil sampler assemblies has been pivotally moved from its stowed position of FIG. 4 to its operative position.
Figure 8:
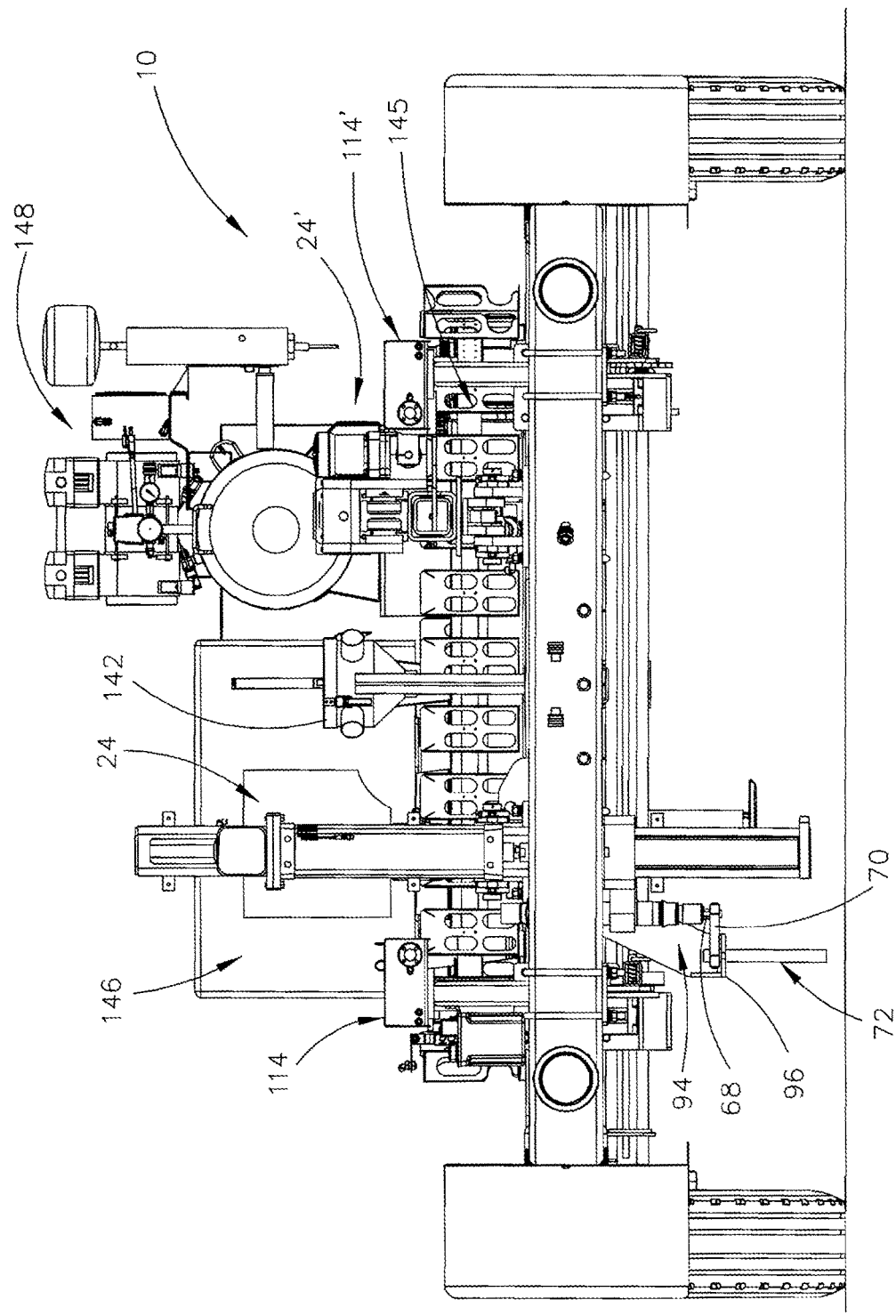
FIG. 8 is a rear view of the soil sampler of this invention wherein one of the soil sampler assemblies is in its operative position.

The numeral 36 refers to a pneumatic cylinder including a barrel 38 having a forward end and a rearward end. Cylinder 36 may be a hydraulic cylinder. A piston rod 40 slidably extends from the rearward end of barrel 38. The forward end of barrel 38 is pivotally secured to crossmember 42 of frame 10 by a pivot pin 44. The outer or rearward end of piston rod 40 of cylinder 36 is pivotally secured to support 26 rearwardly of pivot pin 34. Assuming that support 26 is in its horizontally disposed first position of FIG. 4, the extension of piston rod 40 from barrel 38 of cylinder 36 causes support 26 to be pivoted to its vertically disposed second position of FIG. 7. Retraction of piston rod 40 into barrel 38 of cylinder causes support 26 to be pivoted from its vertically disposed second position of FIG. 7 to its horizontally disposed first position of FIG. 3.

The numeral 46 refers to an elongated generally I-shaped slide rail which is secured to and positioned on the upper end of support 26 at the second end thereof and which has a first end 48 and a second end 50. As seen, the second end 50 of slide rail 46 is positioned adjacent the second end of support 26.

A roller slide 52 is longitudinally movably mounted on slide rail 46 between first and second positions. The numeral 54 refers to an elongated pneumatic cylinder including a barrel 56 having a first end 58 and a second end 60 with a piston rod 62 extending from the second end 60 of barrel 56. Cylinder 54 may be a hydraulic cylinder. The first end 58 of barrel 56 of cylinder 54 is secured to an upstanding post 64 which extends upwardly from support 26 adjacent the first end 28 of support 26. The outer end of piston rod 62 is secured to roller slide 52. The extension of piston rod 62 from barrel 56 of cylinder 54 causes roller slide 52 to be moved towards the second end 50 of slide rail 46. The retraction of piston rod 62 into barrel 56 of cylinder 54 causes roller slide 52 to be moved towards the first end 48 of slide rail 46.

The numeral 66 refers to a conventional air hammer which is secured to the outer side of roller slide 52 for longitudinal movement therewith. Hammer 66 includes a bit, tool, etc. 68 which extends from the chuck thereof. A plate or connector 70 has one end secured to bit 68 and extends transversely therefrom. The outer end of plate 70 is clamped or otherwise secured to an elongated hollow soil probe 72, having a first end 74 (upper) and a second (lower) end 76, adjacent end 74. Air hammer 66 is preferably a Hoteche heavy duty 1½" electric demolition hammer which is rated voltage 110 volt 60H3. The rated power of hammer 66 is 900 watts with a full load impact of 2900 BPM.

The numeral 78 refers to an elongated pneumatic cylinder which includes a barrel 80 having a first end 82 and a second end 84 with a piston rod 86 extending from end 84 of barrel 80. Cylinder 78 could be a hydraulic cylinder. Cylinder 78 is positioned within support 26 and has its first end 82 secured to support 26. A slide member 88 is slidably mounted within support 26 and has a first end 90 and a second end 92. The outer end of piston rod 86 is secured to the first end 90 of slide member 88.

The numeral 94 refers to a pressure foot assembly 94 which has an inner end secured to slide member 88 for movement therewith. Pressure foot assembly 94 includes a portion 96 which extends outwardly through an elongated slot 98 formed in the side of support 26. A pressure foot 100 is provided at the outer end of portion 96 and has a probe opening formed therein which movably receives the soil probe 72 extending therethrough. The extension of piston rod 86 from barrel 80 of cylinder 78 causes pressure foot 100 to be moved away from the second end 30 of support 26. The retraction of piston rod into barrel 80 of cylinder 78 causes pressure foot 100 to be moved away from the second end of support 26.

Figure 17:
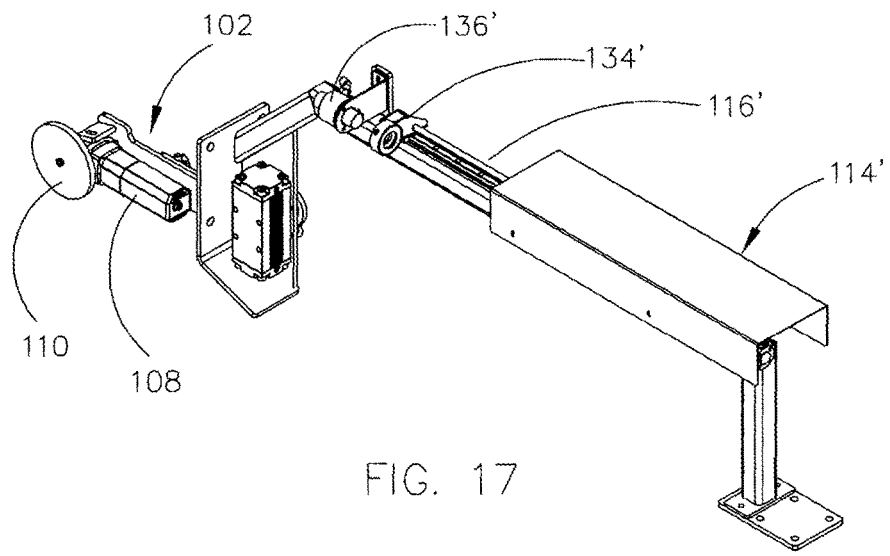
FIG. 17 is a partial perspective view of the trash remover of FIG. 16 in its inoperative position.
Figure 18:
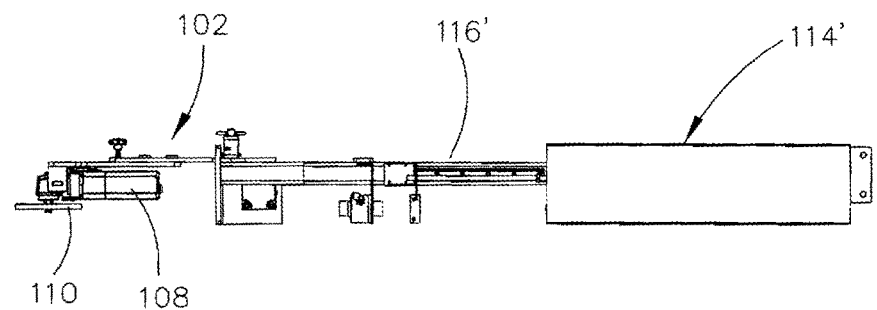
FIG. 18 is a partial top view of the trash remover of FIG. 17.
Figure 19:
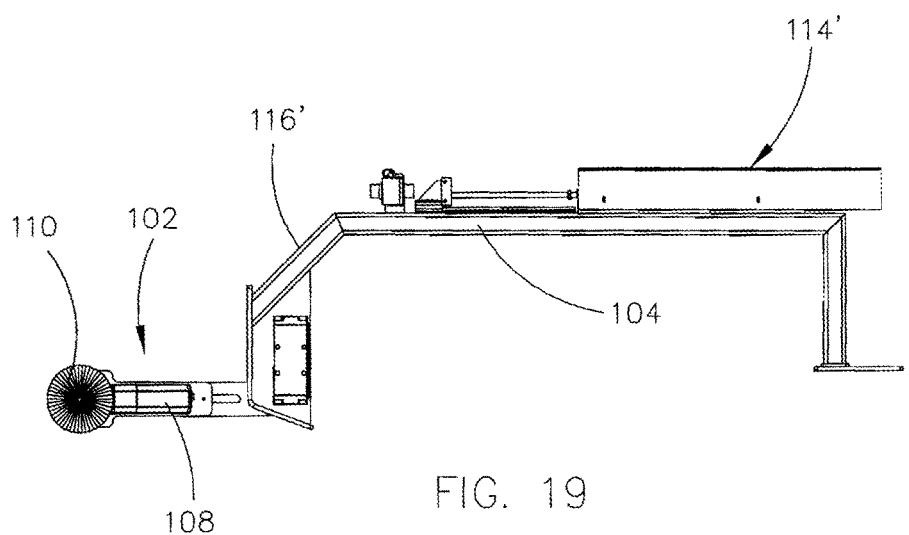
FIG. 19 is a partial side view of the trash remover of FIGS. 16-18.
Figure 20:
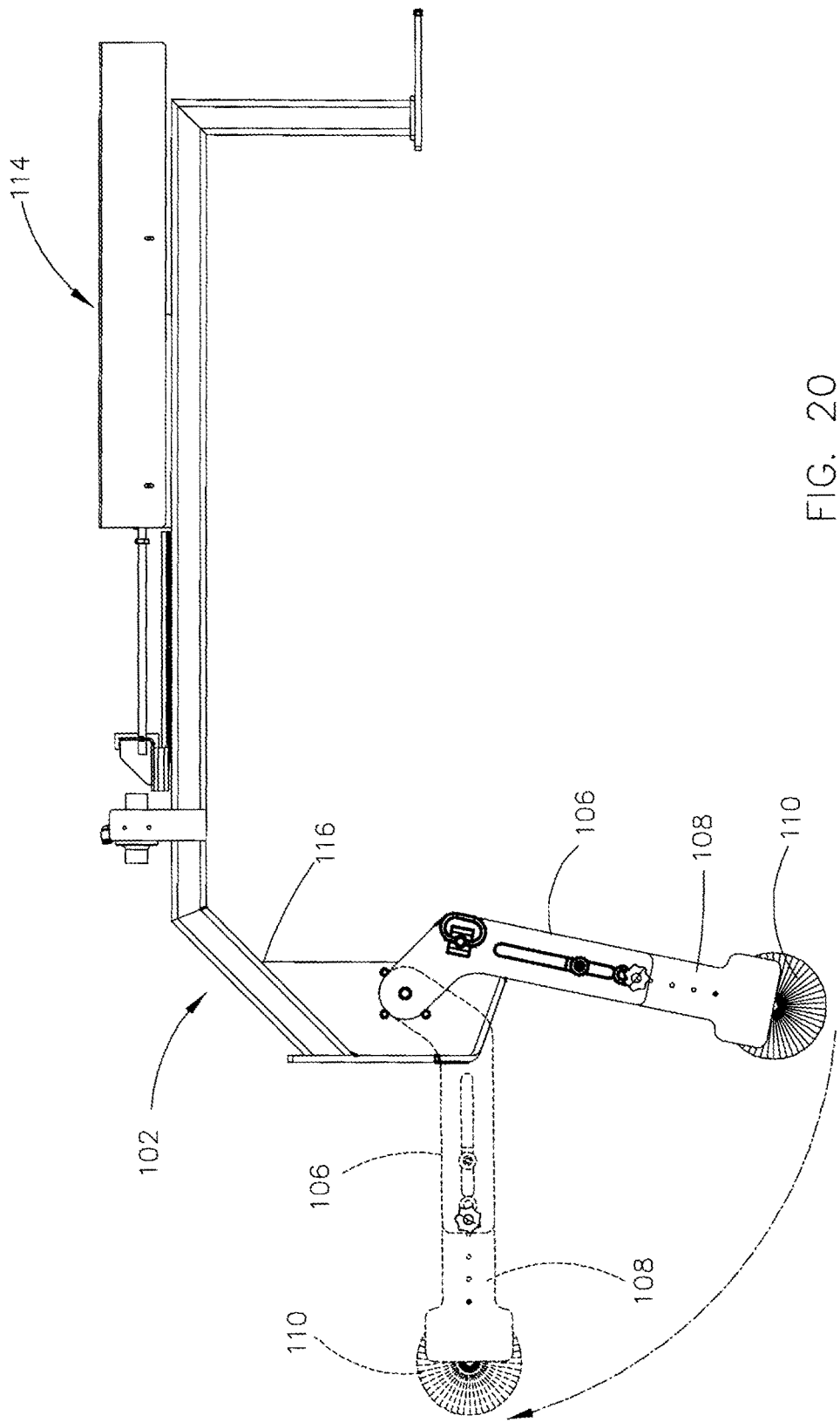
FIG. 20 is a partial side view of the trash remover of FIGS. 16-19.

The numeral 102 refers to an optimal, but preferred, trash cleaner assembly which clears the trash from where the soil sample is to be taken. Assembly 102 includes a support arm 116 which has one end secured to the frame 12 by any convenient manner such as support structure 104. The outer end of arm 116 has a bracket 106 selectively pivotally secured to the rearward end thereof. Bracket 106 is selectively pivotally movable between the inoperative position of FIGS. 17-19 and the operative position of FIGS. 16 and 20. A rotary cleaning wheel support 108 is adjustably secured to the lower end of bracket 106. Cleaning wheel 110 is rotatably secured to support 108 and is electrically or pneumatic rotated by a power source within support 108. The trash cleaning wheel 110 is operated to clean the trash 112 from the area where the soil sample is to be taken. A trash cleaner assembly is positioned forwardly of each of the soil probes 72 and 72 of the soil sampler assemblies 24 and 24'.

The numeral 114 refers to a soil probe cleaner and oiler assembly which is mounted on the support structure 116 which is secured to the frame 12 as seen in FIG. 1. Soil probe cleaner and oiler assembly 114 includes a horizontally disposed pneumatic cylinder 118, which could be a hydraulic cylinder, having a piston rod 120 slidably extending forwardly from the forward end thereof. Piston rod 120 slidably extends forwardly through an oil chamber 122 filled with a lubricating oil. The forward end of piston rod 120 has a brush 124 extending forwardly therefrom.

Soil probe cleaner and oiler assembly 114 also includes a horizontally disposed pneumatic or hydraulic cylinder 126 having a piston rod 128 extending forwardly therefrom. A support 130 is slidably movably mounted on a rail 132 which is secured to support arm 104. A probe cleaning ring 134 is secured to support 130 for movement therewith. Ring 134 embraces soil tube 72 as will be described hereinafter.

Figure 16:
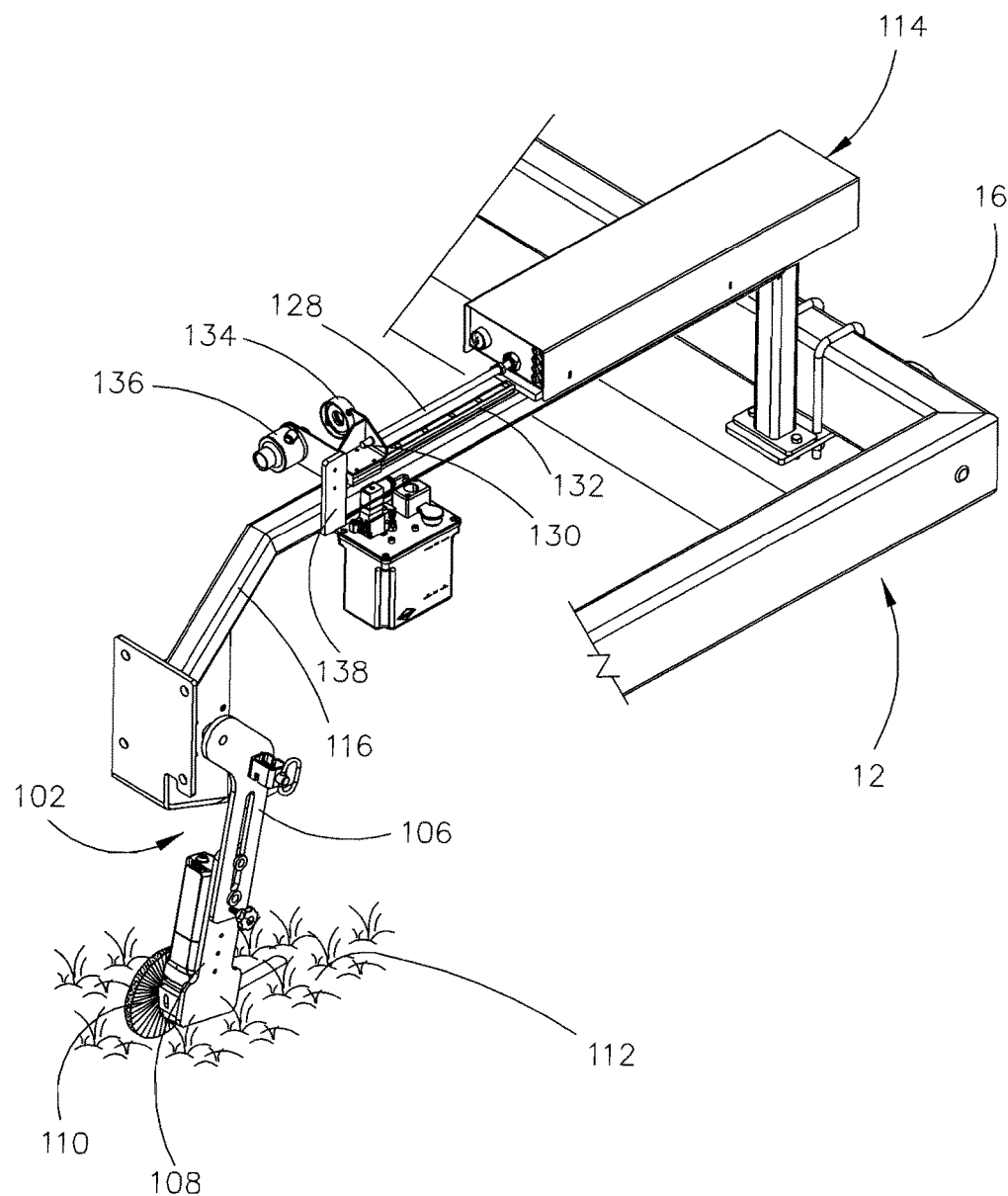
FIG. 16 is a partial perspective view which illustrates one of the trash remover portions of the invention.

A hollow tube 136 is mounted on a support 138 which is fixed to support structure 116. Tube 136 is aligned with cleaning ring 134 as seen in FIG. 16. The rearward end of suction tube 140 is secured to tube 136 and extends forwardly therefrom to a sample collector 142. Collector 142 is configured to discharge soil sampler 143 into bags 144 arranged on a sample collector apparatus 145. The numeral 146 refers to a motor driven generator mounted at the forward end of frame 12. The numeral 148 refers to an air compressor.

The operation of the soil sampler of this invention will now be described. The soil sampler 10 is pulled into the field where the soil samples are to be taken.

During the time that the soil sampler 10 is pulled to the desired location, the soil sampler assemblies 24 and 24' will be in their horizontally disposed stowed or transport positions so as to present a compact soil sampler. When the soil sampler 10 arrives where the soil samples are to be taken, the generator motor or engine 146 will be started. The air compressor 148 will also be started.

Inasmuch as each of the soil sampler assemblies 24 and 24' function identically, only the operation of soil sampler assembly 24 will be described in detail. The optimal trash cleaner assembly 102 is lowered so that the cleaning wheel 110 is in contact with the soil or trash 112 therebelow. The cleaning wheel 110 is then rotated to clear or clean the trash from the area where the soil probe 72 will be driven into the ground. The soil sampler assembly 24 is then pivotally moved upwardly from the horizontally disposed stowed or transport position of FIG. 1 to its vertically disposed position of FIG. 7.

The pressure foot 100 of pressure foot assembly 94 is then lowered into ground engagement by the extension of the piston rod 86 of cylinder 78. The soil probe 72 is then driven into the ground by the extension of the piston rod 62 of cylinder 54 which causes roller slide 52 to move downwardly on slide rail 46. If the ground is very hard, the hammer 66 is activated which hammers the probe 72 into the ground.

As the soil probe 72 is driven into the ground, a soil sample 143 is received therein. When the soil sample has been received in the soil probe 72, the soil probe 72 is raised from ground engagement. The pressure foot 100 is raised to its upper position.

The soil sampler assembly 24 is then pivotally moved from its vertically disposed position to its horizontally disposed position. When the assembly 24 has been raised to its horizontally disposed position, the outer end of soil probe 72 will be aligned with the rearward end of tube 136 which is in suction communication with the rearward end of tube 140. Suction is then applied to tube 140 to suck the soil sample 143 into tube 140 for conveying the sample 143 to the collector 142. However, the sample 143 may stick in soil probe 72. The soil probe cleaner and outer assembly 114 is then actuated. The extension of piston rod 120 from cylinder 118 will cause brush 124 to be pushed into the end of probe 72 to push the sample 143 into the tube 136 where it will be sucked into the tube 140. The brush 124 not only pushes the sample 143 into the tube 136 but will clean the interior of probe 72. The brush 124 will also oil the interior of probe 72. Further, the ring 134 will clean the exterior of probe 72 when cylinder 126 is extended.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. A soil sampler, comprising:

a support frame having a forward end, a rearward end, a first side and a second side;

an elongated first support having a first end and a second end;

said first support being pivotally secured, intermediate its length, to said support frame about a horizontal axis which is transversely disposed with respect to the longitudinal axis of said first support;

said first support being selectively pivotally movable with respect to said support frame between a generally horizontally disposed first position and a vertically disposed second position;

a first pneumatic cylinder including an elongated barrel, with forward and rearward ends, and a piston rod movably extending from said rearward end of said barrel thereof;

said piston rod of said first pneumatic cylinder being movable between extended and retracted positions with respect to said barrel thereof;

said forward end of said barrel of said first pneumatic cylinder being pivotally secured to said support frame;

said piston rod of said first pneumatic cylinder being pivotally secured to said first support;

the extension of said piston rod of said first pneumatic cylinder causing said first support to be pivotally moved from its said first position to its said second position with respect to said support frame;

the retraction of said piston rod of said first pneumatic cylinder causing said first support to be pivotally moved from its said second position to its said first position with respect to said support frame;

an elongated slide rail, having first and second ends;

said slide rail being mounted on said first support at said second end of said first support;

a second pneumatic cylinder including an elongated barrel, with first and second ends, and a piston rod movably extending from said second end thereof;

said first end of said barrel of said second pneumatic cylinder being operatively secured to said first support;

a slide member slidably mounted on said slide rail between first and second positions with respect thereto;

said piston rod of said second pneumatic cylinder being selectively movable between retracted and extended positions with respect to said barrel of said second pneumatic cylinder;

said piston rod of said second pneumatic cylinder being secured to said slide member;

an air actuated hammer device secured to said slide member for movement with said slide member;

said hammer device having a connector element extending therefrom;

said slide member, when said piston rod of said second pneumatic cylinder is in said retracted position, being in said first position;

said slide member, when said piston rod of said second pneumatic cylinder is in said extended position, being in said second position;

an elongated hollow soil probe having first and second ends;

said connector element of said hammer device being secured to said soil probe at said first end of said soil probe whereby movement of said slide member with respect to said first support causes movement of said soil probe between first and second positions;

a soil pressure foot assembly including a flat pressure foot having a soil probe opening formed therein whereby said soil probe extends through said soil probe opening;

a third pneumatic cylinder operatively secured to said first support and said pressure foot for moving said pressure foot between first and second positions;

said pressure foot being in engagement with the soil being sampled when in its said second position and said first support is in its said vertically disposed position;

said soil probe being driven through said soil probe opening in said pressure foot and into the soil to be tested by the extension of said piston rod of said second pneumatic cylinder when said first support is in its said vertically disposed second position and said pressure foot is in engagement with the soil being tested;

said soil probe and the soil sample therein being raised upwardly from the soil being sampled, after said soil probe has been driven into the soil, by the retraction of said piston rod of said second pneumatic cylinder; and a soil sample collection apparatus supported on said support frame for collecting soil samples from said soil probe.

2. The soil sampler of claim 1 further including means for cleaning said soil probe after said soil probe has collected and dispensed a soil sample.

3. The soil sampler of claim 1 further including a trash remover assembly mounted on said support frame for removing trash from the area in which said soil probe is to be inserted into the soil being sampled.

4. The soil sampler of claim 1 further including a soil probe oiler configured to oil the interior of said soil probe after said soil probe has collected and dispensed a soil sample therefrom.

5. A soil sampler, comprising:
a support frame having a forward end, a rearward end, a first side and a second side;
an elongated first support having a first end and a second end;
said first support being pivotally secured, intermediate its length, to said support frame about a horizontal axis which is transversely disposed with respect to the longitudinal axis of said first support;
said first support being selectively pivotally movable with respect to said support frame between a generally horizontally disposed first position and a vertically disposed second position;
a first pneumatic cylinder including an elongated barrel, with forward and rearward ends, and a piston rod movably extending from said rearward end of said barrel thereof;
said piston rod of said first pneumatic cylinder being movable between extended and retracted positions with respect to said barrel thereof;
said forward end of said barrel of said first pneumatic cylinder being pivotally secured to said support frame;
said piston rod of said first pneumatic cylinder being pivotally secured to said first support;
the extension of said piston rod of said first pneumatic cylinder causing said first support to be pivotally moved from its said first position to its said second position with respect to said support frame;
the retraction of said piston rod of said first pneumatic cylinder causing said first support to be pivotally moved from its said second position to its said first position with respect to said support frame;
an elongated slide rail, having first and second ends;
said slide rail being mounted on said first support at said second end of said first support;
a second pneumatic cylinder including an elongated barrel, with first and second ends, and a piston rod movably extending from said second end thereof;
said first end of said barrel of said second pneumatic cylinder being operatively secured to said first support;
a slide member slidably mounted on said slide rail between first and second positions with respect thereto;
said piston rod of said second pneumatic cylinder being selectively movable between retracted and extended positions with respect to said barrel of said second pneumatic cylinder;
said piston rod of said second pneumatic cylinder being secured to said slide member;
an elongated, hollow soil probe having first and second ends;
said soil probe being operatively connected to said slide member for movement therewith;
said slide member, when said piston rod of said second pneumatic cylinder is in said retracted position, being in said first position;
said slide member, when said piston rod of said second pneumatic cylinder is in said extended position, being in said second position;
an elongated hollow soil probe having first and second ends;
said soil probe being driven into the soil to be tested by the extension of said piston rod of said second pneumatic cylinder when said first support is in its said vertically disposed second position;
said soil probe and the soil sample therein being raised upwardly from the soil being sampled, after said soil probe has been driven into the soil, by the retraction of said piston rod of said second pneumatic cylinder;
a soil pressure foot assembly including a flat pressure foot having a soil probe opening formed therein whereby said soil probe extends through said soil probe opening;
a third pneumatic cylinder operatively secured to said first support and said pressure foot for moving said pressure foot between first and second positions;
said pressure foot being in engagement with the soil being sampled when in its said second position and said first support is in its said vertically disposed position; and
a soil sample collection apparatus supported on said support frame for collecting soil samples from said soil probe.

6. The soil sampler of claim 5 further including means for cleaning said soil probe after said soil probe has collected and dispensed a soil sample.

7. The soil sampler of claim 5 further including a trash remover assembly mounted on said support frame for removing trash from the area in which said soil probe is to be inserted into the soil being sampled.

8. The soil sampler of claim 5 further including a soil probe oiler configured to oil the interior of said soil probe after said soil probe has collected and dispensed a soil sample therefrom.

9. A soil sampler, comprising:
a support frame having a forward end, a rearward end, a first side and a second side;
an elongated first support having a first end and a second end;
said first support being pivotally secured, intermediate its length, to said support frame about a horizontal axis which is transversely disposed with respect to the longitudinal axis of said first support;
said first support being selectively pivotally movable with respect to said support frame between a generally horizontally disposed first position and a vertically disposed second position;
a first pneumatic cylinder including an elongated barrel, with forward and rearward ends, and a piston rod movably extending from said rearward end of said barrel thereof;
said piston rod of said first pneumatic cylinder being movable between extended and retracted positions with respect to said barrel thereof;
said forward end of said barrel of said first pneumatic cylinder being pivotally secured to said support frame;
said piston rod of said first pneumatic cylinder being pivotally secured to said first support;
the extension of said piston rod of said first pneumatic cylinder causing said first support to be pivotally moved from its said first position to its said second position with respect to said support frame;

the retraction of said piston rod of said first pneumatic cylinder causing said first support to be pivotally moved from its said second position to its said first position with respect to said support frame;

an elongated first slide rail, having first and second ends;

said first slide rail being mounted on said first support at said second end of said first support;

a second pneumatic cylinder including an elongated barrel, with first and second ends, and a piston rod movably extending from said second end thereof;

said first end of said barrel of said second pneumatic cylinder being operatively secured to said first support;

a first slide member slidably mounted on said first slide rail between first and second positions with respect thereto;

said piston rod of said second pneumatic cylinder being selectively movable between retracted and extended positions with respect to said barrel of said second pneumatic cylinder;

said piston rod of said second pneumatic cylinder being secured to said first slide member;

an air actuated first hammer device secured to said first slide member for movement with said first slide member;

said first hammer device having a connector element extending therefrom;

said first slide member, when said piston rod of said second pneumatic cylinder is in said retracted position, being in said second position;

said first slide member, when said piston rod of said second pneumatic cylinder is in said extended position, being in said second position;

an elongated and hollow first soil probe having first and seconds;

said connector element of said first hammer device being secured to said first soil probe at said first end of said first soil probe whereby movement of said first slide member with respect to said first support causes movement of said first soil probe between first and second positions;

an elongated second support having a first end and a second end;

said second support being spaced from said first support at one side of said first support;

said second support being pivotally secured, intermediate its length, to said support frame about a horizontal axis which is transversely disposed with respect to the longitudinal axis of said second support;

said second support being selectively pivotally movable with respect to said support frame between a generally horizontally disposed first position and a vertically disposed second position;

a fourth pneumatic cylinder including an elongated barrel, with forward and rearward ends, and a piston rod movably extending from said rearward end of said barrel thereof;

said piston rod of said fourth pneumatic cylinder being movable between extended and retracted positions with respect to said barrel thereof;

said forward end of said barrel of said fourth pneumatic cylinder being pivotally secured to said support frame;

said piston rod of said fourth pneumatic cylinder being pivotally secured to said first support;

the extension of said piston rod of said fourth pneumatic cylinder causing said second support to be pivotally moved from its said first position to its said second position with respect to said support frame;

the retraction of said piston rod of said fourth pneumatic cylinder causing said second support to be pivotally moved from its said second position to its said first position with respect to said support frame;

an elongated second slide rail, having first and second ends;

said second slide rail being mounted on said second support at said second end of said second support;

a fifth pneumatic cylinder including an elongated barrel, with first and second ends, and a piston rod movably extending from said second end thereof;

said first end of said barrel of said fifth pneumatic cylinder being operatively secured to said second support;

a second slide member slidably mounted on said second slide rail between first and second positions with respect thereto;

said piston rod of said fifth pneumatic cylinder being selectively movable between retracted and extended positions with respect to said barrel of said fifth pneumatic cylinder;

said piston rod of said fifth pneumatic cylinder being secured to said second slide member;

an air actuated second hammer device secured to said second slide member for movement with said second slide member;

said second hammer device having a connector element extending therefrom;

said second slide member, when said piston rod of said fifth pneumatic cylinder is in said retracted position, being in said second position;

said second slide member, when said piston rod of said fifth pneumatic cylinder is in said extended position, being in said second position;

an elongated hollow second soil probe having first and second ends;

said connector element of said second hammer device being secured to said second soil probe at said first end of said second soil probe whereby movement of said second slide member with respect to said second support causes movement of said second soil probe between first and second positions;

said second soil probe being driven into the soil to be tested by the extension of said piston rod of said fifth pneumatic cylinder when said second support is in its said vertically disposed second position;

said second soil probe and the soil sample therein being raised upwardly from the soil being sampled, after said soil probe has been driven into the soil, by the retraction of said piston rod of said fifth pneumatic cylinder;

a second soil pressure foot assembly including a flat second pressure foot having a soil probe opening formed therein whereby said second soil probe extends through said soil probe opening in said second pressure foot;

a fifth pneumatic cylinder operatively secured to said second support and said second pressure foot for moving said second pressure foot between first and second positions;

said second pressure foot being in engagement with the soil being sampled when in its said second position and said second support is in its said vertically disposed position; and a soil sample collection apparatus supported on said support frame for collecting soil samples from said second soil probe.

* * * * *